United States Patent [19]

White

[11] Patent Number: 5,030,230
[45] Date of Patent: Jul. 9, 1991

[54] CORNEAL IMPLANT

[75] Inventor: Thomas C. White, Sioux Falls, S. Dak.

[73] Assignee: Great Plains Eye Clinic, Ltd., Sioux Falls, S. Dak.

[21] Appl. No.: 460,839

[22] PCT Filed: Sep. 19, 1988

[86] PCT No.: PCT/US88/03207

§ 371 Date: Jan. 23, 1990

§ 102(e) Date: Jan. 23, 1990

[87] PCT Pub. No.: WO89/05128

PCT Pub. Date: Jun. 15, 1989

Related U.S. Application Data

[63] Continuation-in-part of Ser. No. 130,748, Dec. 9, 1987, Pat. No. 4,772,283, which is a continuation-in-part of Ser. No. 864,002, May 16, 1986, abandoned.

[51] Int. Cl.⁵ .................................................. A61F 2/14
[52] U.S. Cl. ........................................................ 623/5
[58] Field of Search ......................................... 623/4, 5

[56] References Cited

U.S. PATENT DOCUMENTS

| | | | |
|---|---|---|---|
| 4,676,790 | 6/1987 | Kern | 623/5 |
| 4,772,283 | 9/1988 | White | 623/5 |
| 4,908,404 | 3/1990 | Benedict et al. | 525/54.11 |

Primary Examiner—Alan W. Cannon
Attorney, Agent, or Firm—James R. Haller; Gregory P. Kaihoi; Mary P. Bauman

[57] ABSTRACT

An implant prosthesis and method for replacing a full or partial thickness of a cornea. The prosthesis includes a transparent lens portion, and a carrier of preserved tissue, preferably cornea. The lens is attached to the carrier which in turn is adapted for attachment to the eye wall.

5 Claims, 5 Drawing Sheets

CORNEAL IMPLANT

RELATED APPLICATIONS

This application is a continuation-in-part of co-pending U.S. patent Application Ser. No. 130,748, filed Dec. 9, 1987, now U.S. Pat. No. 4,772,283 which in turn was a continuation-in-part of U.S. patent application Ser. No. 864,002, filed May 16, 1986, now abandoned.

FIELD OF THE INVENTION

This invention relates to prosthetic devices and methods, and particularly to such devices and methods as may be employed to replace and/or repair damaged corneal tissue.

BACKGROUND OF THE INVENTION

A variety of pathological and accidental causes give rise to damage to the cornea of the eye. Corneal ulceration and resultant scarring are among the most frequent causes of loss of vision worldwide. Ulceration can result from infections, as with Pseudomonas, Staghglococcus, Herpes, and fungi, as well as from chemical and thermal burns, including sometimes after thermokeratoplasty. Ulceration can also occur in association with severe vitamin A and protein deficiency (keratomalacia); in certain "dry eye" conditions, and in neuroparalytic keratitis; in eyes of patients with autoimmune disease apparently limited to the cornea (Mooren's ulcer), and in association with known systemic autoimmune disorders, like lupus erythematosus and Wegener's granulomatosis, and possible autoimmune diseases like rheumatoid arthritis. Ulceration sometimes progresses to actual perforation with the formation of synechiae between iris and cornea, secondary glaucoma, and even blindness due to death of the optic nerve. Usually, however, after serious insult to the cornea and enzymatic erosion of the stromal matrix, ulceration is arrested, and the cornea, like injured skin, forms scar tissue which scatters light, causing loss of visual acuity. Other mechanical damage can also occur to the cornea, as from scratches or punctures by foreign objects. For these and a variety of other reasons, the corneal portions of eyes must be surgically repaired or replaced.

As ulceration (resulting in scarring and consequent loss of visual acuity) is a primary concern in most corneal damage, either as the result of one of the above diseases or as a side effect of other traumatic injury to the eye, prevention or mitigation of ulceration in the above situations will usually minimize or eliminate scarring and the attendant loss of vision. It is believed that ulceration is the result of local release of proteolytic enzymes—collagenase and other proteases. Likely, these enzymes are released by polymorphonuclear leukocytes, although other cell types may also contribute. Upon severe inflammation of the anterior segment, leukocytes leak out from the dilated conjunctival capillaries into the tear film. If there is an epithelial defect of the cornea, the leukocytes appear to attach to the naked stromal surface, and there release their proteolytic enzymes, causing digestion of the corneal tissue. Mechanical protection of the epithelial defect, as by gluing on a contact lens, appears to be effective in preventing such ulceration. See generally, C. Dohlman, "Biology of Complications following Keratoprosthesis," Cornea 2: 175–76 (1983); and M. Berman, "Collagenase and Corneal Ulceration," in *Collagenase in Normal and Pathological Tissue*, D. Wooley and J. Evanson, eds., John Wiley & Sons, Ltd., New York (1980). This technique is not always possible or effective, however, particularly in the case of keratoprostheses, as typical adhesives usable in vivo, such as cyanoacrylate, form only a temporary bond at best, which is eventually degraded by tears and/or necrosis.

Corneal transplants are often necessary for a variety of reasons, including repair of an opacified cornea after an ulcer has healed by forming scar tissue. Such transplants have become quite common in the United States, particularly with the advent of microsurgery. Unfortunately, donor corneas are very difficult to obtain. A cornea to be donated must be employed, if at all, within a matter of days or weeks from the time of death of the donor. Although eye banks have been organized throughout the United States, one cannot rely upon the availability of a donor at the time it is needed for a transplant operation. As a result, vision which could have been wholly or partially restored in many patients often is lost permanently. Furthermore, some diseases are not amenable to standard corneal transplants, and corneal transplants carry the constant risk of transmission of diseases carried in the transplanted tissue, including leukemia, syphilis, and Acquired Immunodeficiency Syndrome (AIDS). See Fuji Kawa, et. al., "Human T-Cell Leukemia/Lymphotrophic Virus Type III in the Conjunctival Epithelium of Patient with AIDS," 100 *Amer. J. Opthal.* 507 (Oct. 1985); Pepose et. al., "The Impact of the AIDS Epidemic on Corneal Transplantation," 100 *Amer. J. Opthal.* 610 (Oct. 1985).

Attempts have been made in the past to utilize artificial materials for corneal transplants. Representative of such attempts are those reported in Barraquer, *Queratomileusis y Queragofaquia, Instituto Barraquer de America Bogata, Col.* (1980); U.S. Pat. No. 3,945,054, issued Mar. 23, 1976, Fedorov, et. al., "Through Corneal Prosthesis and Method of Installing Same"; and U.S. Pat. No. 3,458,870, issued Aug. 5, 1969, W. Stone, Jr., "Artificial Corneal Implants Having a Removable Lens Member."

For the most part, the implantation of artificial corneal materials has been at best a temporary stop gap measure taken to seal the anterior chamber of the eye for a period of time until a donor cornea could be located for transplantation. As with other parts of the human body, the eye tends to reject and eject or extrude foreign materials during the healing process, with the result that the implantation of artificial corneas generally leads to loss by extrusion of the device, to further eye damage and to leakage of aqueous humor from the anterior chamber. Attempts to affix artificial corneas to the cornea by adhesive typically fail because the living cells contacted by adhesive eventually die and slough off (necrosis), destroying the adhesive seal. Thus, the prior art devices have relied on elaborate mechanical attachment methods which are fraught with continued need for surgical revision, and have had short-lived, limited success.

SUMMARY OF THE INVENTION

The invention relates to an ocular implant prosthesis having a transparent lenticule, and a carrier bonded thereto, the carrier comprising preserved tissue adapted for attachment to an eye. The prosthesis optionally may replace the full thickness of the eye wall, a partial thickness, or be placed on the surface of Bowman's membrane after removal of the epithelium. In one embodiment, the carrier comprises an annular ring, the outer periphery thereof being adapted for attachment to the eye wall, and the inner circumferential surface thereof being bonded to the transparent lenticule. In another embodiment, the lenticule is bonded to the anterior surface of the carrier. In a further embodiment, the lenticule is bonded to the posterior surface of the carrier. In yet a further embodiment, the carrier includes a generally disc shaped pocket coaxial with the carrier, the pocket being adapted to receive there within the lenticule. The preserved tissue may be any suitable tissue, but preferably is cornea, sclera, fascia, cartilage, tendon, or bone.

The invention also relates to a method of surgically repairing the cornea of an eye, comprising the steps of removing at least a partial, generally circular thickness of the eye wall, including corneal tissue; providing an ocular prosthesis having a transparent lenticule of biologically acceptable material bonded to a carrier, the carrier comprising preserved tissue adapted for attachment to the eye wall; and surgically attaching the carrier to the eye wall covering the area from which tissue was removed.

The use of preserved tissue provides great advantages over the prior art in that such tissue may be bonded to any suitable lenticule material. Because the tissue itself is preserved, its cells will not be adversely affected by the adhesive, and therefore are not subject to necrosis. Another advantage of the preserved tissue is that it will become durably attached to the live tissue of the eye through in-growth of live fibroblastic cells from the patient recipient into the structural matrix of the preserved tissue. Further, the tissue may be preserved in such a fashion as to absolutely prevent the transmission of diseases from the preserved tissue source to the recipient.

In a particularly preferred embodiment, the lenticule is attached to the tissue carrier by an adhesive bond, the adhesive preferably being comprised of an adhesive polyphenolic protein, such as the type derived from the mussel genus *Mytilus*. The use of polyphenolic protein provides great advantages over many other adhesives which are prone to hydrate and/or adhesively fail when continuously exposed to water. Indeed, the mussel from which the protein is derived uses such polyphenolic proteins to permanently adhere to a variety of surfaces under sea water, with adhesion strengths in excess of about $10^2$ lb/in$^2$ (about $10^6$ N/m$^2$). In yet another embodiment the tissue carrier is merely the polyphenolic protein itself, polymerized as the lenticule is attached to the cornea.

Further, the invention relates to a method of surgically repairing the cornea of an eye, comprising the steps of removing at least a partial, generally circular thickness of the eye wall, including corneal tissue; and attaching an ocular prosthesis having a transparent lenticule of biologically acceptable material to the eye wall covering the area from which tissue was removed. The attachment step is accomplished by applying to the lenticule or the cornea, or both, polymerizable adhesive polyphenolic protein such as the type derived from the mussel genus *Mytilus*, and then polymerizing the protein to form a permanent adhesive bond therebetween.

BEST MODE FOR CARRYING OUT THE INVENTION

Figures 1, 2:
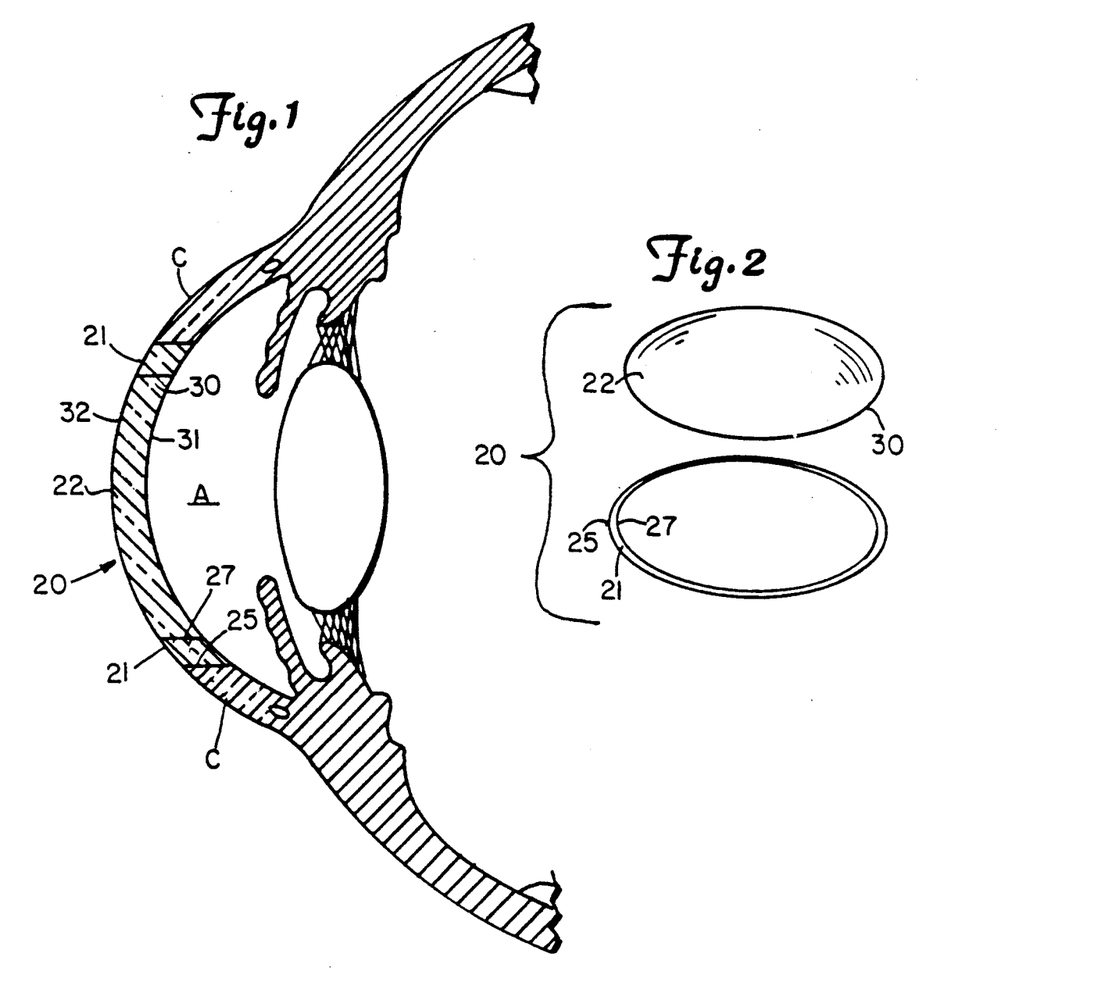
FIG. 1 is a cross sectional view of the human eye showing a prosthesis of the invention implanted.
FIG. 2 is a perspective exploded view of a corneal prosthesis of the invention.
Figure 3:
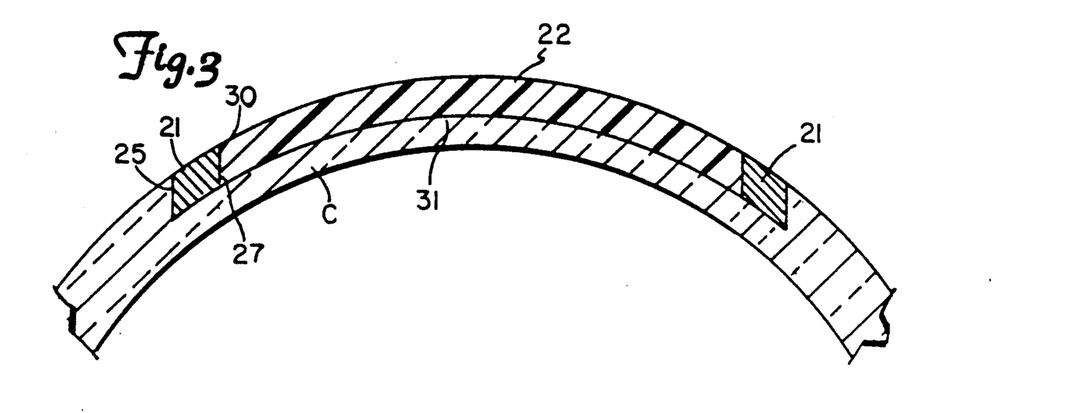
FIG. 3 is a partial cross-sectional view of the cornea of an eye showing lamellar implant of a modified embodiment of the invention.

FIGS. 1 and 2 depict a prosthesis of the invention generally as 20, including a central transparent lenticular portion 22 and a carrier 21. The prosthesis may be mounted in the eye as a corneal replacement as shown in the drawings, the carrier 21 spacing the lenticular portion 22 radially from the eye tissue.

The lenticule 22 may be made of any of a variety of suitable materials, including polymethyl methacrylate (PMMA), polycarbonates, HEMA, polysulfones, silicones and other substances that are biologically acceptable, not introducing harmful foreign substances into the eye. The lenticule 22 desirably has a slightly domed anterior surface 32 to simulate the natural curvature of the surgically removed corneal portion. Its posterior surface 31 may be configured as desired—convex, planar or concave. The lenticule 22 may be so configured as to act as a lens and to provide visual correction for the eye by varying the curvatures of the posterior 31 and anterior 32 surfaces.

The carrier 21 is constructed of biologically derived tissue. The tissue may be of any suitable material, including cornea, sclera, fascia or other connective tissues such as tendon, cartilage or bone. Corneal tissue is preferred for those embodiments shown in the drawing which require the carrier 21 to be transparent, for example, FIGS. 6–13, and 15. The tissue preferably is preserved in a fashion which generally maintains the structural integrity of the extra-cellular collagen architectural matrix. Such preservation processes include but are not necessarily limited to glycerin dehydration, alcohol preservation, gluteraldehyde preservation, and formalin preservation. Preferably the preservation process denatures the tissue, analogously to tanning of rawhide, resulting in a number of benefits as described below.

In a preferred method of preserving such tissue, biological tissue, such as sclera, is removed, cleaned, and placed into preservative such as gluteraldehyde or formalin, where it may be stored for a period of days, weeks, or even months. When desired, the tissue is removed from the preservative and, if not already in proper configuration, manufactured into the appropriate configuration. The tissue is then united with the artificial lenticule as described herein, and the resulting prosthesis is placed in a preservative that is compatible with the lenticule material such as formalin. It should be noted that some lenticule materials, such as PMMA, are incompatible with alcohol, but are compatible with other preservatives such as formalin, which is therefore a particularly preferred storage medium for the manufactured prosthesis.

Desirably the preservative denatures the tissue. Denaturing may alter the antigenicity of the tissue to reduce or eliminate rejection complications, and in certain circumstances may permit use of biological tissue from other species. Denaturing also may tend to inhibit vascularization, a particularly desirable effect if the tissue is cornea. In most instances, the tissue is stored at least about three days in the preservative before use.

Manufacture of tissue into the appropriate physical configurations shown in the drawings can be accomplished by well known techniques including the use of microkeratomes and trephines. See, e.g., Kaufman, "The Correction of Aphakia," 89 *American Journal of Ophthalmology*, 1 (Jan. 1980); Leigh, "Treatment of Gross Corneal Opacification by Lamellar and Annular Lamellar Keratoplasty," 39 *Brit. J. Ophthal.* 641 (1955); Waring, *Refractive Keratoplasty*, 31 Resident & Staff Physician, 25–34 (May, 1985).

FIG. 1 depicts the carrier 21 as having an outer periphery 25 and an inner circumferential surface 27 generally defined by coaxial cylinders. Other configurations may also be utilized, but the generally coaxially parallel configuration shown in FIG. 1 is particularly desirable due to its ease of manufacture using a trephine. Similarly, the periphery 30 of the lenticule 22 has a surface defined by a cylinder coaxially of the lenticule axis, thus providing surface-to-surface contact with the inner circumferential surface 27 of the carrier 21.

Figure 14:
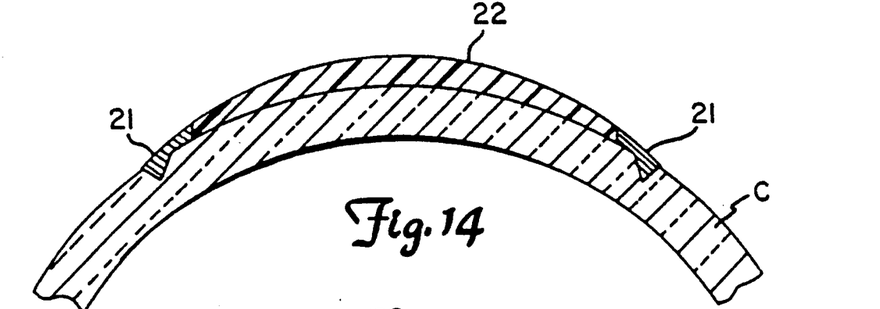
FIG. 14 is a partial cross-sectional view of the cornea of an eye showing lamellar implant of a modified embodiment of the invention.
Figure 15:
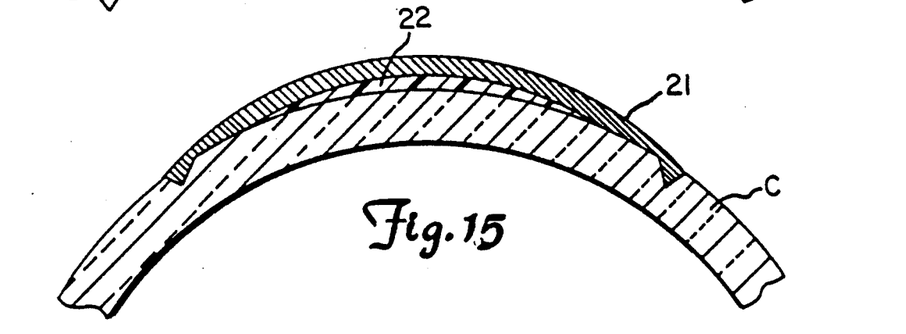
FIG. 15 is a partial cross-sectional view of the cornea of an eye showing lamellar implant of a modified embodiment of the invention.

FIG. 1 depicts replacement of the full thickness of the cornea (C). FIG. 2 depicts lamellar keratoplasty, i.e., replacement of only a partial thickness of the cornea (C). This technique has the advantage of not destroying the natural liquid seal of the cornea, and avoiding disruption of intraocular structures while replacing diseased or abnormal anterior corneal tissue. FIGS. 14–15 depict epikeratoplasty, i.e., placement of the prosthesis on the deepithelized surface of the cornea. Epikeratoplasty is particularly useful in the correction of myopia and hyperopia, as well as keratoconus and as a patch for perforations.

The lenticule 22 may be attached to the preserved tissue carrier 21 by any suitable means, including but not limited to any of a variety of biologically acceptable adhesives. Such adhesives must be characterized by their ability to form a liquid-tight bond between the material of the lenticule 22 and the preserved tissue carrier 21. Among adhesives suitable for this purpose are various well known dental adhesives. In particular, applicant has used an adhesive sold by Johnson & Johnson under the product number 2748. This two-part adhesive has successfully bonded both formalin and gluteraldehyde preserved tissue to a polymethyl methacrylate lenticule.

A particularly preferred class of adhesives are the bioadhesive polyphenolic proteins, such as that derived from the mussel genus *Mytilus*. These adhesives are characterized by a very low aqueous dispersive effect probably due, at least in part, to the high amounts of hydroxyproline (Hyp) and 3,4-dihyroxyphenylalanine (Dopa) present in the proteins. These adhesives have very low solubility at neutral or slightly basic pH, and adhere to many substrates, including biological substrates, durably in the presence of water, apparently for many years. They are particularly preferred for their long term durability under wet/humid conditions, for their ability to be applied to a wet substrate, and for their ability to bond durably to collagenous substrates. Furthermore, as they are biologically derived adhesives, they are likely to be biologically compatable in most forms.

These bioadhesive proteins may be isolated from the phenol glands of mussels according to well known techniques, including those described in Waite and Tanzer, *Science*, 212, 1038 (May 21, 1981); and U.S. Pat. No. 4,496,397, "Process for Purifying and Stabilizing Catechol-Containing Proteins and Materials Obtained Thereby," J. Waite (Jan. 29, 1985).

Such polyphenolic proteins appear to be characterized by including repeating decapeptide units having the following chemical formula:

PRO/HYP  PRO/HYP  SER/THR  TYR/DOPA  LYS where each X is either hydroxyl or hydrogen, and each R is either hydrogen or methyl.

Such decapeptides may be prepared and isolated according to the methods reported in U.S. Pat. No. 4,687,740, "Decapeptides Produced From Bioadhesive Polyphenolic Proteins," J. Waite (Aug. 18, 1987). Furthermore, such decapeptides may be polymerized to form large polyphenolic molecules having up to 1000 such repeating units, the linking group being an amino acid, an oligopeptide or a bifunctional spacer, as set forth in U.S. Pat. No. 4,687,740. European Pat. Application No. 87105775, published Nov. 11, 1987 (EP 244688) reports preferred adhesive formulations prepared utilizing such polyphenolic proteins. The formulations include the decapeptide unit, either singly or in polymerized form, together with a crosslinking agent (such as mushroom tyrosinase) and additional optional additives such as surfactants (such as SDS) and filler (such as collagen). Other methods for manufacturing such polyphenolic proteins are described in European Pat. Application No. 87104853 (published as EP 242656, Oct. 28, 1987), and A. C. Jouanneau, "A New Bio-Adhesive: A Protein Extract of Mussels—Attempts to Produce This Adhesive from *Mytilus Edulis* by Genetic Engineering," Biofutur (41, 65-66) 1985 (French). From the foregoing, it is seen that such bioadhesive polyphenolic proteins may be obtained through isolating them from natural producers of the proteins (i.e., the mussels themselves), or by synthesizing or genetically engineering them through standard techniques. Furthermore, as the unique adhesive properties of these proteins are believed to result from the presence of Dopa and hydroxyproline, certain changes in the remaining molecular structure of the proteins, likely including some amino acid substitutions (probably other than the Dopa and Hyp units), are likely to be possible to control and/or select properties of the bioadhesive.

Figure 16:
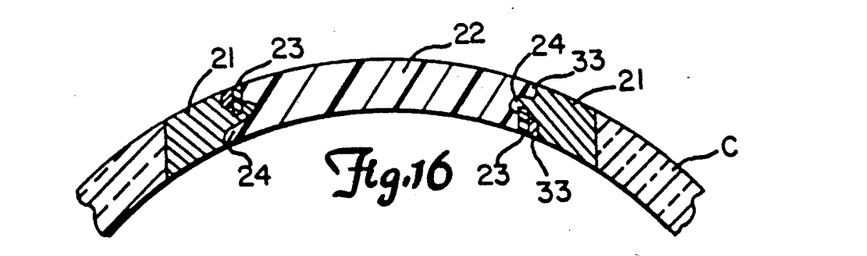
FIG. 16 is a partial cross-sectional view of the cornea of an eye showing a modified embodiment of the invention.
Figure 17:
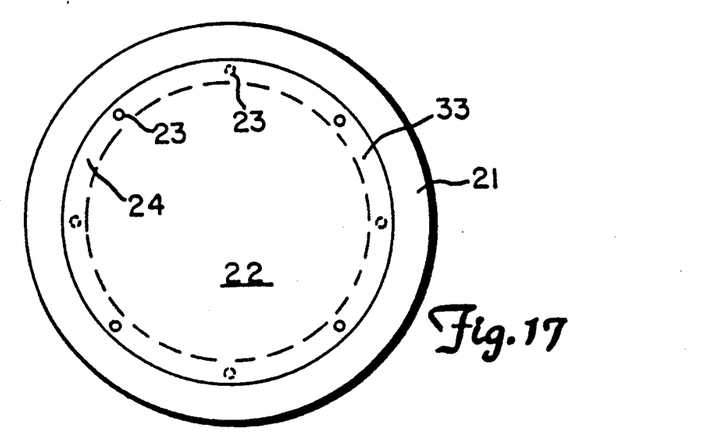
FIG. 17 is a plan view of the embodiment of FIG. 16.

Other methods of bonding the lenticule to the preserved tissue may be utilized, including the use of heat and pressure. FIGS. 16 and 17 depict a method of attaching the carrier to the lenticule 22. In this embodiment, the carrier 21 includes a radially inwardly extending flange 24 received in a complimentary groove in the peripheral edge of the lenticule. A plurality of axially extending stakes 23 are positioned about the periphery of the lenticule, the stakes 23 being driven at least part way through from one side of the lenticule into the flange 24 of the carrier 21. Desirably the stakes penetrate at least half way through the tissue flange 24.

To assemble such a prosthesis, the tissue may be rehydrated and placed about the lenticule. Stakes are then driven into place and, e.g., heat fused to the lenticule, the stakes desirably being of the same material as the lenticule. The unit is then placed in preservative, which frequently causes slight tissue shrinkage, resulting in a firm seal between the carrier 21 and the lenticule 22.

The drawing shows eight generally equi-angularly spaced stakes. Any suitable number may be utilized, so long as enough are used to avoid undue stress on tissue surrounding any one stake. The stakes may be inserted from alternate sides of the lenticule, as shown in the drawings, or they may be inserted from a single side. If inserted from a single side, it is desirable that the stakes pass entirely through the carrier flange 24, thus being anchored in both opposing flanges 33 of the lenticule 22.

As an alternative to such stakes 23, the tissue may be retained in the peripheral groove of the lenticule by other similar mechanical means. Such means may comprise crimping the two flanges 33 of the lenticule to pinch and retain the carrier flange 24, either at selected points along the periphery of the lenticule (spaced similarly to the depicted spacing of the stakes 23) or along a continuous circumference. Point crimping may be preferred over continuous crimping, as the latter tends to deform the periphery of the lenticule more than point crimping.

Figure 4:
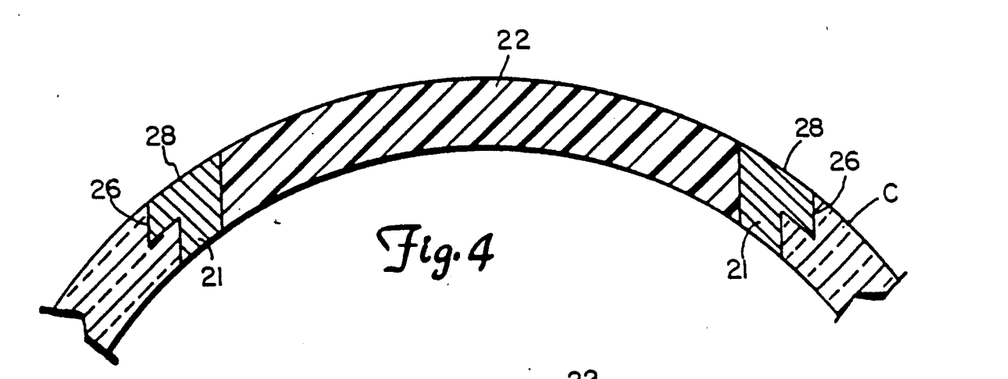
FIG. 4 is a cross-sectional view of a cornea showing a modified embodiment of the invention implanted.
Figures 5, 6:
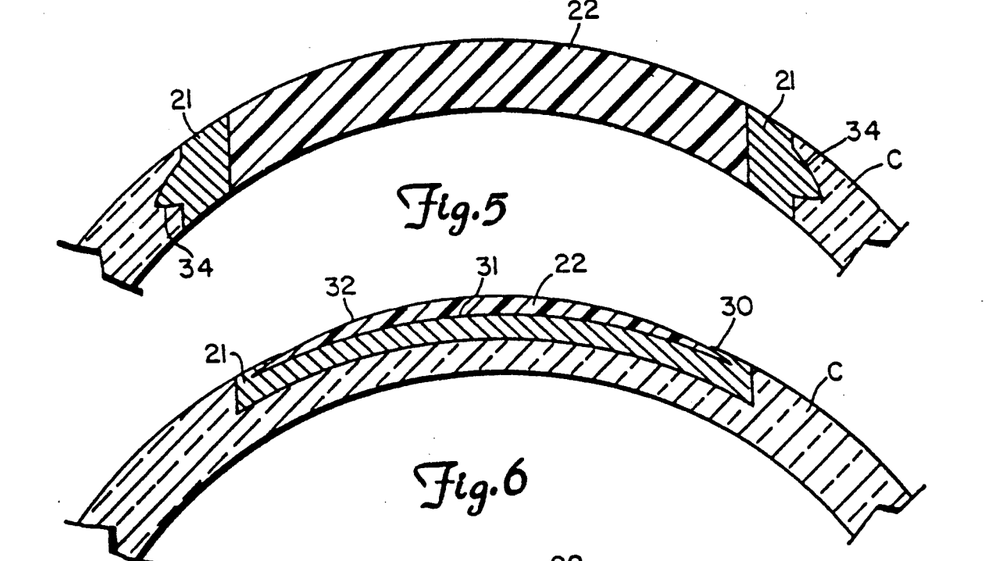
FIG. 5 is a cross-sectional view of a cornea showing a modified embodiment of the invention implanted.
FIG. 6 is a partial cross-sectional view of the cornea of an eye showing lamellar implant of a modified embodiment of the invention.

FIGS. 4 and 5 depict, by way of example and not by way of limitation, alternative embodiments for the attachment of the carrier 21 to the cornea (C). In FIG. 4, the carrier is provided with a radially outwardly extending flange 26 at its anterior surface 28. The flange 26 is received in a complimentary groove formed in the cornea (C). This configuration is desirable for its natural structural assistance in placement of the prosthesis during surgery.

FIG. 5 similarly shows a carrier having a radially outwardly extending flange 34 which is located approximately equidistant from the anterior and posterior surfaces of the prosthesis. The flange 34 is received within a complimentary annular groove formed in the cornea (C). Many of a variety of structural variations might be made to enhance attachment, including those described in my U.S. application Ser. No. 402,740, now U.S. Pat. No. 4,612,012. Similarly, the lenticule 22 may include flanges, protrusions, or other structural features to enhance attachment of the lenticule 22 to the carrier 21, e.g., as described above. For the sake of clarity in the drawings, such structural features are not shown in a number of the drawings.

The carrier 21 is easily sutured or adhesively bonded (as by utilizing the polyphenolic protein adhesives described above) to the cornea (C), as the carrier is quite durable. The interstices within the carrier's collagen matrix, which are not substantially affected by the preferred denaturization, permit host-tissue cells to migrate and grow therein, laying down new collagen which interdigitates to form a "living bond" between the carrier 21 and the cornea (C). The carrier 21 may be of any suitable radial thickness, desirably at least 1 mm to provide sufficient tissue for suturing, and preferably between about 1.5 mm and about 3 mm. As described below, however, the carrier 21 may be substantially larger.

FIGS. 6–9 show various alternative embodiment of the invention wherein the carrier comprises a disk having a diameter slightly larger than the diameter of the lenticule 22. In FIG. 6, the lenticule 22 is bonded to the carrier 21 which in turn is attached to the cornea (C), initially by sutures and/or adhesive, and eventually by tissue in-growth. This embodiment has the advantage of completely isolating the lenticule from contact with the cornea (C) and the anterior chamber (A). Desirably the peripheral edge of the lenticule 22 is "buried" within the carrier 21 to inhibit growth of epithelium between the two portions of the prosthesis.

Figure 7:
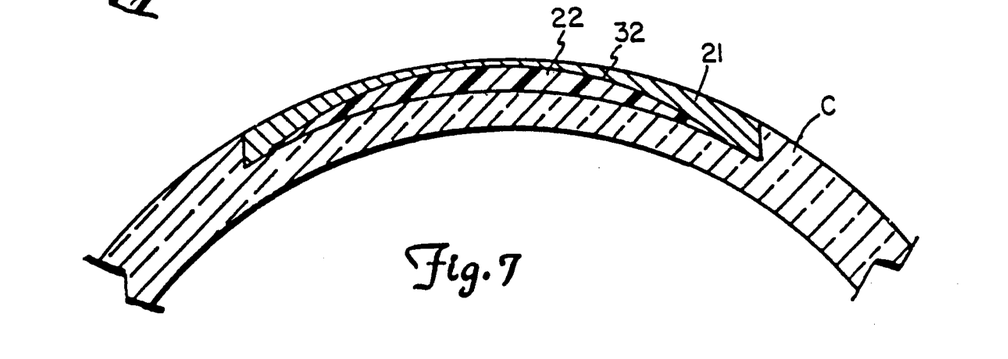
FIG. 7 is a partial cross-sectional view of the cornea of an eye showing lamellar implant of a modified embodiment of the invention.
Figure 8:
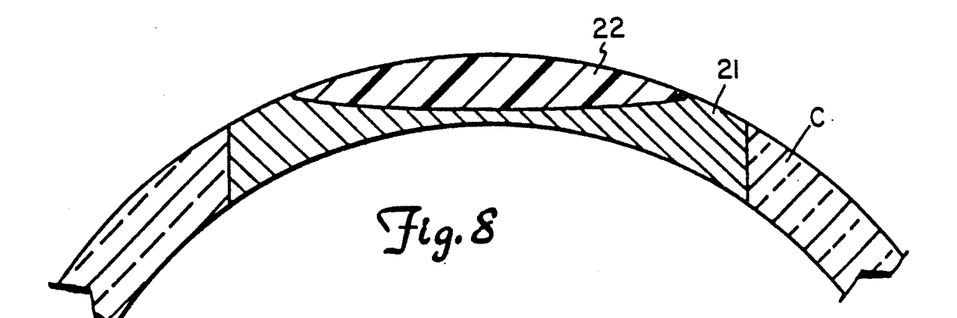
FIG. 8 is a cross-sectional view of a cornea showing a modified embodiment of the invention implanted.
Figure 9:
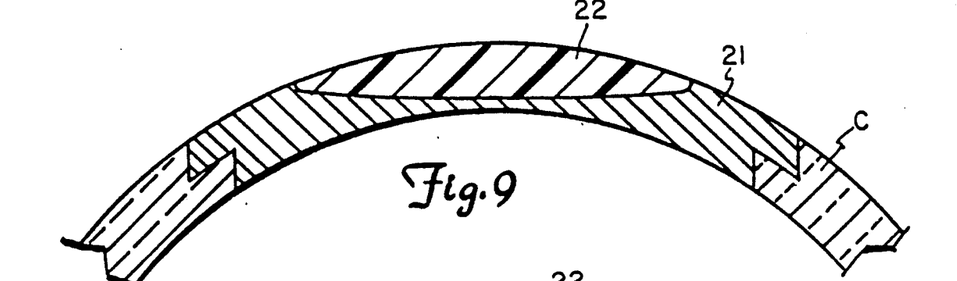
FIG. 9 is a cross-sectional view of a cornea showing a modified embodiment of the invention implanted.

In FIG. 7, the lenticule 22 is held between the carrier 21 and the cornea (C). Similar variations are shown in FIGS. 8 and 9, in which a full thickness of cornea (C) has been removed. It will be recognized that in each of the embodiments shown in FIGS. 6–9, the carrier must be comprised of a tissue which is and remains transparent, i.e., preferably corneal tissue.

Figure 10:
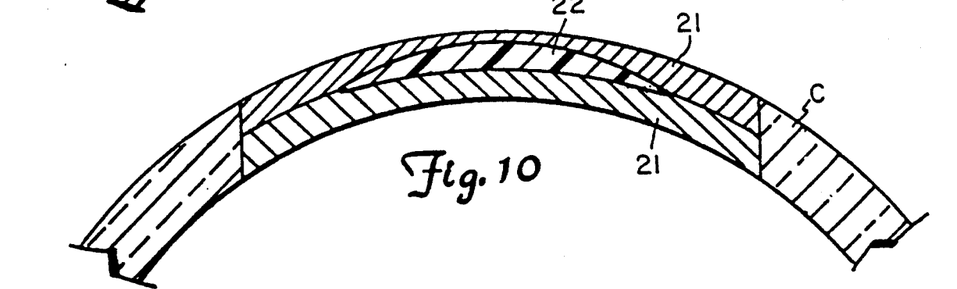
FIG. 10 is a cross-sectional view of a cornea showing a modified embodiment of the invention implanted.
Figure 11:
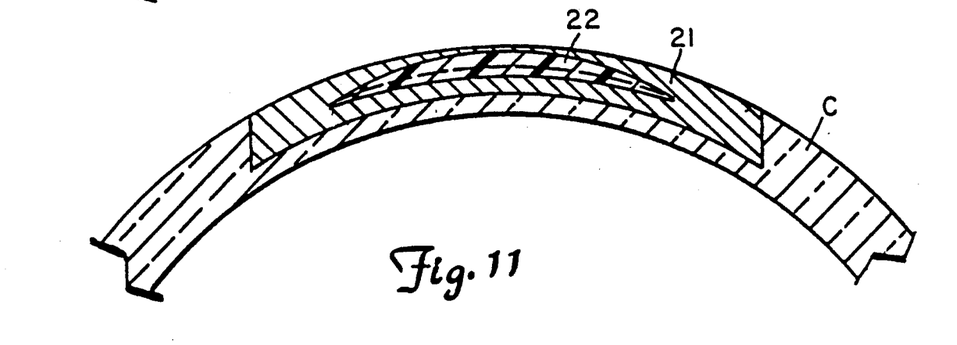
FIG. 11 is a partial cross-sectional view of the cornea of an eye showing lamellar implant of a modified embodiment of the invention.
Figure 12:
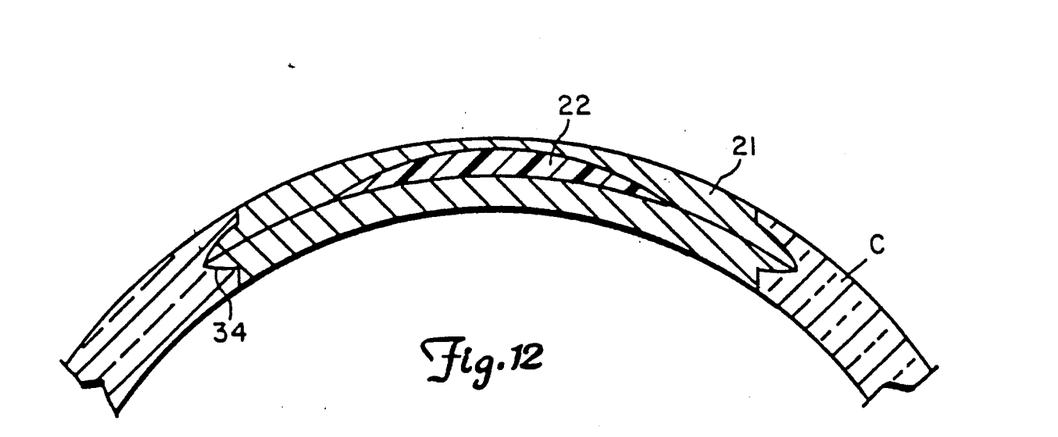
FIG. 12 is a partial cross-sectional view of the cornea of an eye showing lamellar implant of a modified embodiment of the invention.
Figure 13:
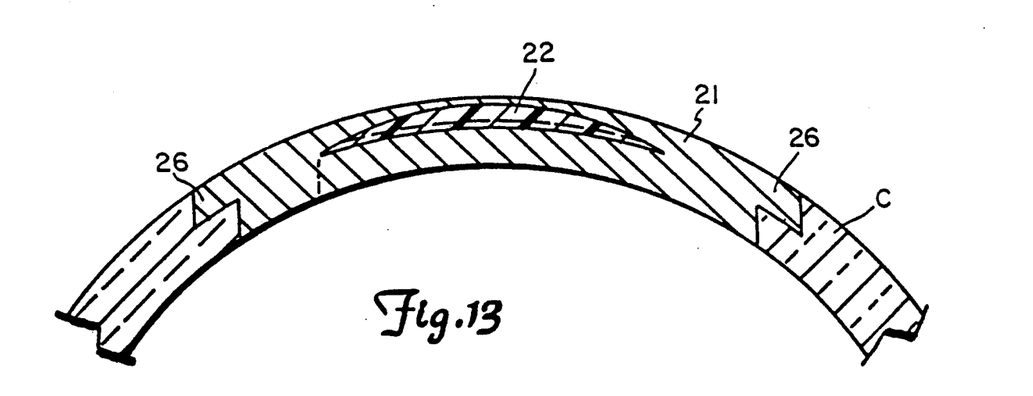
FIG. 13 is a partial cross-sectional view of the cornea of an eye showing lamellar implant of a modified embodiment of the invention.

FIGS. 10–13 show alternative embodiments in which the lenticule 22 is "sandwiched" between layers of the carrier 21. In such embodiments, the carrier may be comprised of two pieces, as shown in FIG. 10, which are optionally bonded, sutured or otherwise fastened together, or alternately the carrier may include a pocket, as shown in FIGS. 11–13, cut so as to receive the lenticule 22 therein. The pocket configuration may be created by known techniques, such as those described in Choyce, "Polysulfone Corneal Inlays to Correct Refractive Errors," *Cataract* 6 (Jun. 1985). Although the "sandwich" technique of FIGS. 10–13 introduces an additional optical interface, it has the advantage of providing a Bowman's membrane which may be re-populated by the recipient's epithelium. Furthermore, this configuration reduces the risk of ingrowth of epithelium between the preserved tissue and the lenticule. Note that these advantages also apply to the embodiment of FIG. 7.

FIGS. 14–15 depict epikeratoplasty, i.e., placement of the prosthesis on the deepithelized Bowman's membrane of the cornea (C), as described above. Although not depicted in the drawings, protheses of the invention employing the "sandwich" or "pocket" techniques previously described, as well as other modifications of the structural variations shown, may be used in epikeratoplasty.

The surgical methods which are employed for implantation of the prosthesis of the invention are to be very carefully performed, often through the aid of a microscope as is the case with surgical procedures involving donor corneal transplants, nerve reattachments, and other types of microsurgery, and the preparations for surgery and the surgical tools employed in the method of the invention are identical or similar to those employed in a donor corneal transplant surgery.

Prior to surgery, the diameter of the corneal or epithelial section to be removed from the eye is determined, leaving a sufficient amount of cornea or corneoscleral rim material to enable the prosthesis of the invention to be implanted. Also prior to surgery the prosthesis of the invention is made ready for implantation by suitable sterilization procedures. If desired, the prosthesis may be fabricated at or shortly prior to the time of surgery so that the correct sizing to the individual patient may be accomplished. Alternately the prosthesis may be prefabricated in a number of sizes. The diameter of the peripheral portion of the prosthesis, measured across its outer periphery, should be the same as or slightly larger than the diameter across the tissue rim remaining after removal of the corneal portion. Should the patient be a child, care is generally taken to make the diameter of the corneal rim as small as practicable so that, as the child grows, the prosthesis of the invention may be replaced with larger prostheses while still maintaining the field of the implant within the bounds of the corneo-limbus, subsequent implant procedures ordinarily involving the removal of a small portion of the previously formed corneal rim.

In the implant procedure, the eye is immobilized and the corneal portion to be removed is excised employing suitable instruments such as a trephine of the type normally used in corneal transplant procedures. Upon completion of the removal of the corneal tissue, the prosthesis of the invention is inserted into the circular space defined by the rim of the cornea. During the procedure, the prosthesis is supported by a suitable handle or grip such as a small suction cup applied to the outer, domed surface of the lenticule 22. Desirably, small sutures are taken about the periphery of the carrier 21 and are passed through the cornea to anchor the carrier 21 in place. Alternatively or in addition, a suitable adhesive such as a bioadhesive polyphenolic protein may be applied to the mating surfaces to securely bond them. The generally tight fit between the carrier and the corneal tissue rim assures that no leakage of aqueous humor from the eye will occur. Post operative procedures are similar to those commonly employed in corneal transplant surgery.

In another application of the invention, a prosthesis of the invention may be implanted within a pocket surgically formed in the recipient's cornea according to the procedures set forth in Choyce, "Polysulfone Corneal Inlays to Correct Refractive Errors," *Cataract*, 7 (June 1985). In this technique, no cornea is removed, but a pocket is dissected in the cornea and the prosthesis may then be inserted into the pocket. The carrier need not be sutured to the cornea; the preserved tissue will gradually be ingrown as described above, firmly fixating the prosthesis.

While a preferred embodiment of the present invention has been described, it should be understood that various changes, adaptations and modifications may be made therein without departing from the spirit of the invention and the scope of the appended claims.

What is claimed is:

1. An ocular implant prosthesis having a transparent lenticule, a carrier comprising preserved tissue adapted for attachment to an eye, and a bioadhesive polyphenolic protein bonding the carrier to the lenticule.

2. The prosthesis of claim 1 wherein the polyphenolic protein is of the type derived from the mussel genus *Mytilus*.

3. An ocular implant prosthesis having a transparent lenticule made of biologically acceptable material, a carrier comprising an annular ring of preserved, denatured biological tissue, the outer periphery of said annular ring being adapted for attachment to the eye wall, and a bioadhesive polyphenolic protein bonding the inner circumferential surface of the carrier to the lenticule.

4. A method of surgically repairing the cornea comprising the steps of:

(a) removing at least a partial, generally circular thickness of the eye wall;
(b) attaching to an ocular prosthesis having a carrier of preserved, denatured biological tissue a transparent lenticule by forming a radially inwardly extending flange on the carrier and inserting the flange into a complimentary groove in the outer periphery of the lenticule; and
(c) surgically attaching the ocular prosthesis to the eye wall, covering the area from which tissue was removed.

5. A method of surgically repairing the cornea comprising the steps of:
(a) removing at least a partial, generally circular thickness of the eye wall; and
(b) bonding a transparent lenticule to a carrier of preserved, denatured biological tissue of an ocular prosthesis by applying a thin layer of bioadhesive polyphenolic protein therebetween; and
(c) surgically attaching the ocular prosthesis to the eye wall, covering the area from which tissue was removed.

* * * * *